(12) United States Patent
Spehr (10) Patent No.: US 7,926,358 B2
(45) Date of Patent: Apr. 19, 2011

(54) METHOD FOR TESTING FATIGUE OF A LEAD

(75) Inventor: Paul Richard Spehr, Medford, NJ (US)

(73) Assignee: MetaCure Limited, Hamilton (BM)

( * ) Notice: Subject to any disclaimer, the term of this patent is extended or adjusted under 35 U.S.C. 154(b) by 302 days.

(21) Appl. No.: 12/010,396

(22) Filed: Jan. 24, 2008

(65) Prior Publication Data

US 2008/0178684 A1 Jul. 31, 2008

Related U.S. Application Data

(60) Provisional application No. 60/897,867, filed on Jan. 29, 2007.

(51) Int. Cl.
*G01N 3/20* (2006.01)
(52) U.S. Cl. .............................. 73/851; 73/849
(58) Field of Classification Search ............. 73/849–851
See application file for complete search history.

(56) References Cited

U.S. PATENT DOCUMENTS

| | | | | |
|---|---|---|---|---|
| 2,910,863 | A * | 11/1959 | Hornbostel et al. | 73/159 |
| 3,238,756 | A * | 3/1966 | Coffin, Jr. | 72/232 |
| 3,911,713 | A * | 10/1975 | Vydrin et al. | 72/205 |
| 4,244,203 | A * | 1/1981 | Pryor et al. | 72/205 |
| 4,291,562 | A * | 9/1981 | Orr | 72/205 |
| 4,369,791 | A | 1/1983 | Friedman | |
| 4,403,499 | A * | 9/1983 | Sack et al. | 73/158 |
| 4,717,581 | A | 1/1988 | Robblee | |
| 5,654,030 | A | 8/1997 | Munshi et al. | |
| 6,550,323 | B1 * | 4/2003 | Nguyen et al. | 73/158 |
| 2008/0262584 | A1 * | 10/2008 | Bottomley et al. | 607/119 |

OTHER PUBLICATIONS

Iguchi et al. "Fatigue Property of Stainless Steel FES Electrode in Hank's Solution" International FES Symposium Jun. 24-26, 2002. pp Paper available online <http://www.ifess.org/ifess02/stimulation_technology/IguchiY.pdf> Program available online <http://web.archive.org/web/20020723032043/http://robo.fe.uni-lj.si/ifess2002/final3.pdf>.*
Merchant et al. "Strain Controlled Mechanical Fatigue of Thing Copper Foil and Flexible Circuit" IPC EXPO 2001, Apr. 2001. <http://www.gould.com/zope0221/gould/content/e4/e139/e197/tpyear203/tpdownload223/STRAIN_eng.PDF>.*
Lewandowski et al. Tension and Fatigue Behavior of 316LVM 1X7 Multi-strand Cables Used As Implantable Electrodes Materials Science and Engineering: A 486, 2008. Available online Nov. 17, 2007. <http://www.sciencedirect.com/science?_ob=MImg&_imagekey=B6TXD-4R53T11-8-W&_cdi=5588&_user=2502287&_orig=search&_coverDate=07%2F15%2F2008&_sk=995139998>.*
Minnesota Department of Health. "Lab Testing for Mumps" Online Mar. 2010. Accessed Jul. 2, 2010. <http://www.health.state.mn.us/divs/idepc/diseases/mumps/hcp/labtesting.pdf>.*

* cited by examiner

*Primary Examiner* — Harshad Patel
*Assistant Examiner* — Jonathan Dunlap (57) ABSTRACT

A method and apparatus for testing the fatigue of an implantable lead by simultaneously bending and un-bending it at a plurality of successive positions wherein the bending and un-bending positions comprise a substantial length of the lead and wherein the bending radius and sector angle are substantially optional.

27 Claims, 5 Drawing Sheets

METHOD FOR TESTING FATIGUE OF A LEAD

RELATED APPLICATION

This application claims the benefit of U.S. Provisional Patent Application No. 60/897,867 filed on Jan. 29, 2007. The contents of which are hereby incorporated by reference.

FIELD OF THE INVENTION

This invention relates to fatigue testing of leads designated for implantation in a body. Particularly, but not limited to, it relates to testing of abdominal leads at a plurality of locations thereof.

BACKGROUND OF THE INVENTION

Implanted leads for stimulation and sensing of organs are used for many years in various anatomical locations. Typical applications are in cardiac pacemakers and more recently spinal pain relief and control of gastro-internal symptoms and processes.

In the latter context, leads are implanted in the abdomen and attached, for example, to the stomach wall where they are subjected to conditions of tension and varying bending over a considerable distance (~6 cm) while conducting current from a pulse generator. These conditions may contribute to a failure, or fatigue, of the lead due to mechanical stresses and, possibly, corrosion.

As with other implantable devices, the lead's safety and reliability are highly important. An approach to verify a lead's safety and reliability is to subject it to conditions that simulate, or exceed, its operating conditions in the body and to ascertain its functional compliance to specified criteria.

Such an approach is found in BS EN 45501-2-1. This is an established standard for testing pacemaker leads, where various characteristics of their operation is simulated and tested, typically one, or two at a time.

As to mechanical fatigue, the standard specifies bending and un-bending a dry lead at room temperature around a curved corner. One test defines bending in a range of ±90° with bend radius of ~6 mm where a section of ~9 mm, with minimal tension, undergoes 47,000 bending cycles at a rate of 2 Hz. In order to test the relevant part of the lead, the procedure may have to be repeated separately for each of its unique flexible parts.

Another test, for the fatigue of the interface between the lead and its connector, specifies bending in a range of ±45° with a bend radius of ~0.5 mm, where a section of less than 1 mm undergoes 82,000 bending cycles at a rate of 2 Hz, with an applied tension of 100 gr.

Thus, even according to the first test procedure that tests the lead's body fatigue, the bending of a single segment of 9 mm length requires over 6.5 hours.

Another procedure is described in patent GB 878 401. This reference teaches wrapping a wire around two semi-circular 'rockers', which bend and un-bends the wire in alternate directions as the rockers oscillate against each other in reciprocal orientations.

In both of the last two references, the bending section length and bend curvature are mutually related; that is, the tighter the bend the smaller the bent section, and vise versa, the larger the section the shallower the bend.

SUMMARY OF THE INVENTION

A lead fatigue test in the context of the invention relates to repeated bending and un-bending of a lead and inspecting whether it is still operational and undamaged after a specific number of repetitions under specific conditions.

An aspect of some embodiments of the invention relates to testing the fatigue of a lead by simultaneously bending and un-bending it at a plurality of successive positions along the lead and repeating the successive bending a number of times.

In some exemplary embodiments of the invention, the length of the lead subject to bending and un-bending covers approximately the whole length of the lead. Optionally, it comprises a substantial part of the lead length. Optionally, it is approximately the length of the bent part of the lead in the body. Optionally, the length of several leads, before they are cut to sections appropriated for an intended use, is subject to the bending and un-bending.

The lead length is, optionally, approximately 6 cm. Optionally or alternatively, the lead length is 2 cm, 4 cm, 8 cm, 10 cm, 15 cm, 20 cm, 35 cm or 50 cm or intermediate values.

Optionally, the extent of the lead subject to simultaneous bending and un-bending comprises a plurality of sections. Optionally, the sections are tested concurrently. Optionally, the sections may overlap, at least partially.

The invention, as illustrated in some exemplary embodiments, enables to perform a fatigue test in practically short time.

For example, bending a length of 6 cm (typical for abdomen) for 47,000 cycles at a rate of 2 Hz (parameters described for the prior art) will require about 6.5 hours, and that without concurrent bending of different sections. This is contrary to the prior art that bends a small section at a time (such as 9 mm), so that repeating it to bend a length of 6 cm will require nearly two days and nights, which might render it prohibitive for routine testing.

In some exemplary embodiments of the invention, there is substantially no mutual relation between the bending curvature and the bending length, allowing to test long lengths in short times, as described above, while bending the lead around tight curvatures. This approach is contrary to the prior art where the length-curvature relationship obliges prolonged test times when a large section is to be tested by bending around a small radius.

In some exemplary embodiments of the invention, the bending radius and arc angle are maintained at specific values; optionally the radius and arc angle may be set to any value that is representative of the expected stress on the lead.

In some embodiments of the invention, the lead is subject during the fatigue test to conditions approximately simulating, or exceeding, the conditions of its usage. Higher stress conditions may accelerate the aging process and shorten the simulation time, or the lead tolerance to such conditions may indicate its reliability level The environmental stress conditions may comprise one or more of the following options as listed below.

(a) A tension is applied to the lead during the bending.
(b) A bending section of the lead is immersed in a solution.
(c) The lead is subject to electric voltage and current (if applicable)
(d) The lead is maintained at a specific temperature Optionally, a condition, or a combination of conditions, may be applied to a part of the bending section of the lead; to a substantial length of the bending section of the lead; to a substantial length of the lead; or to substantially the entire length of the lead.

In exemplary embodiments of the invention, such a condition, or a combination of conditions, may be applied for one or more portions of the test duration; optionally it may be applied for the entire test duration.

According to an aspect of some embodiments of the invention, more than one portion of the lead is bent simultaneously. Optionally, successive portions are bent in opposite directions.

In exemplary embodiments of the invention, a lead is bent around a specific sector of a roller of a specific average diameter. Optionally, a plurality of rollers may be employed where separate sections of the lead are simultaneously bent and un-bent around sectors of different rollers; optionally the plurality of rollers are of the same or different diameter; optionally the respective bending sectors are the same or of different angles. The plurality of optional dissimilar rollers allow to simultaneously bend and un-bend the lead in different bending directions, curvatures and angles.

In some exemplary embodiments of the invention, the lead is at least partially wrapped about a roller. Optionally the roller is moved such that successive sections of the lead bend and un-bend; optionally the roller is moved to bend and un-bend the lead; optionally the rollers are rotated to bend and un-bend the lead; optionally the rollers rotate and move on the lead to bend and un-bend it.

Optionally and additionally, successive sections of the lead are, at least partially, wrapped about a plurality of rollers such that successive sections of the lead bend and un-bend in one or more directions. Optionally, the lead sections bend and un-bend as the rollers are moved; optionally as the lead is moved; optionally as the rollers rotate. Optionally, a plurality of rollers may bend and un-bend the same region of the lead, in one or more directions.

Optionally in exemplary embodiments of the invention, a plurality of leads is simultaneously subject to a fatigue test.

Optionally, in exemplary embodiments, the bending and un-bending is repeated along a substantial lead length; optionally the bending and un-bending is repeated in alternating directions along at least one region of the lead.

In some exemplary embodiments of the invention, rolling of the rollers along the lead, or the lead movement against rolling (revolving) rollers, is replaced by correspondingly slipping the rollers along the lead or slipping the lead against the rollers; optionally, rolling and slippage may be combined. Optionally one or more rollers are not rotating.

In the specifications and the claims, the term 'lead' relates, but not limited, to electrical conductive leads exemplified by leads implanted in the abdomen for gastric stimulation and sensing, and other implantable leads where bending along a substantial length is expected such as when the generator or the detector are relatively far from the target organ.

Additionally in the specifications and the claims, the term 'roller' relates, in addition to rollers with a circular cross-section, to a cylinder with any profile shape that can perform the functions of the embodiments, without damaging the lead, for example, a cylinder with an elliptical or egg-shape profile.

DETAILED DESCRIPTION OF EMBODIMENTS OF THE INVENTION

Figure 1:
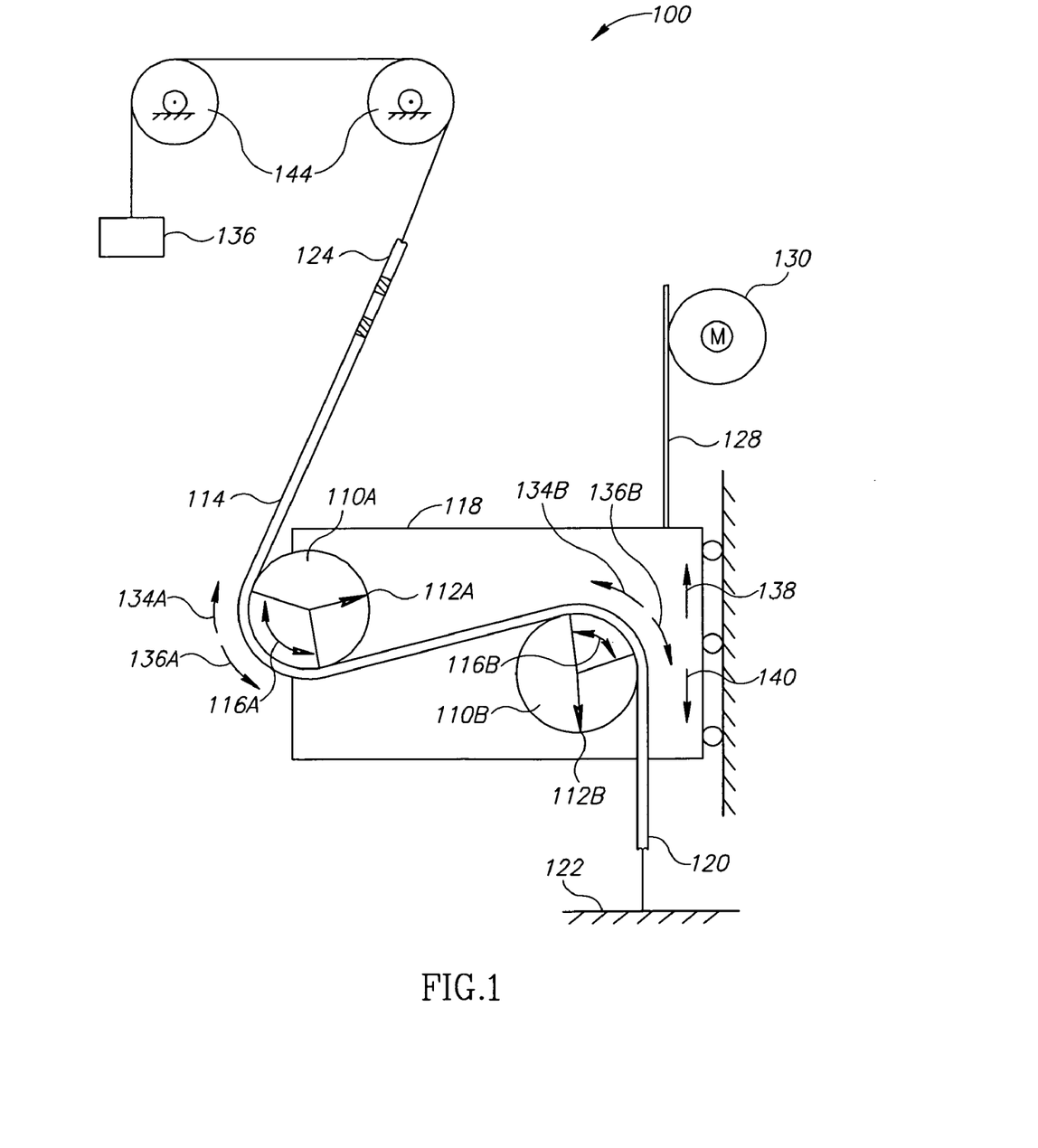
FIG. 1 is a schematic illustration of a mechanical apparatus for testing lead fatigue, in accordance with an exemplary embodiment of the invention where a bending roller is moved along a lead section.

FIG. 1 schematically shows a lead bending apparatus 100 according to an exemplary embodiment of the invention.

Exemplifying one or more rollers, rollers 110a and 110b, with respective radii 112a and 112b, are mounted on frame 118 on axes about which they can rotate. A lead 114 is wrapped about the rollers such that a segment of the lead is wrapped around sector 116a of roller 110a, and another segment on sector 116b of roller 110b.

The lead is kept in sufficient tension to maintain a non-sliding contact with the rollers by securing one end of the lead 120 to a base 122 and pulling the other end 124 by weight 136 with the necessary load via pulleys 144.

Frame 118 is movable in directions 138 or 140 by motor 130 via a linkage member 128. When the frame moves, the rollers turn and roll on the lead, compelling it to bend and un-bend about sectors analogous to 116a and 116b. Specifically, as one part of a lead region comes in contact with a roller, it wraps and bends it while a corresponding part of the lead that leaves contact with the roller un-wraps from the roller contact and straightens.

As a roller moves, bending and un-bending occur at successive positions along a section of the lead. These positions, respective to each roller, may coincide, at least partially, to comprise an extended bending section.

More specifically, when frame 118 moves in direction 138, roller 110a rotates about direction 136a and roller 110b about direction 136b; when frame 118 moves in the opposite direction 140, roller 110a rotates in opposite direction 134a and roller 110b in opposite direction 134b.

Moving frame 118 in alternating directions 138 and 140 describes a bending/un-bending cycle.

The bending/un-bending cycles may be repeated, optionally substantially at the same positions, the repetition comprising a fatigue test.

The cycle rate optionally relates to the expected average or maximal bending rate in the body; optionally the rate is higher than the expected average or maximal bending rate in the body; optionally the rate is based on other factors; optionally the rate may vary during the test; optionally the rate is limited by the apparatus.

Optionally the cycle repetitions relate to the expected average or maximal number of bends in the operational lifetime of the lead; optionally the repetitions exceed the expected average or maximal bends; optionally or additionally, the number of repetitions is based on other factors. Optionally and alternatively, the repetitions are halted if a certain condition is met, such as lead operational failure or fracture.

Optionally, the maximal bending radius of a roller by which the lead is expected to yield to stress may be estimated by calculations based on approximating formulas and physical data of the lead.

Examples for such bending radius estimations based on mechanical properties of coiled wire conductors are:

| Lead/ conductor | Wire diameter (mm) | Coil Pitch (Turns/mm) | Coil diameter (mm) | Radius (mm) |
|---|---|---|---|---|
| CENELEC standard coil | 0.2286 | 1.93 | 0.6858 | 1.45 |
| TIZER ™ | 0.127 | 1.667 | 0.381 | 7.36 |

(CENELEC and TIZER are terms known in the lead industry)

Thus, the maximal bending radius by which the lead is expected to fatigue for representative lead of the industry are in the range of several millimeters.

Optionally, a radius suitable for practical testing time may be determined empirically. Optionally, the radius is the expected average or minimal bending radius of a working lead in the body; optionally it is smaller than the minimal expected radius. Optionally or additionally, the radius may be set due to other factors, for example, the intended or test environment, bending repetition rate or testing time.

Optionally and additionally, the weight 136 is set to maintain a tension in the lead, which is greater than required for a non-skid contact with the rollers. Alternatively or additionally, other appliances may be used to apply the tension, such as elastic strip or spring. Optionally, other methods may be used to apply the non-skid contact between the lead and the roller, for example, a pressure on the lead against the roller such as by an elastic element.

Optionally, the tension applied to the lead relates to the average or maximal tension as expected in the body; optionally the tension exceeds the expected average or maximal tension in the body; optionally or additionally, the tension varies during the bending.

Optionally and additionally, at least a part of the bending section of the lead is immersed in a solution during at least part of the test. Optionally the solution is isotonic saline; optionally it comprises ingredients of the intended environment of the lead; optionally the solution composition is approximately equivalent to the intended environment of the lead; optionally the concentration of possibly harmful components is higher than that of the intended environment; optionally or additionally, the solution comprises other ingredients.

Optionally and/or additionally, when a stimulation lead is tested, the lead is subject to electric voltage and current during at least part of the test. Optionally the electric current is in a pulse waveform; optionally and additionally, the current waveform and intensity are approximately as used for stimulation in the intended operation of the lead. Optionally the voltage or current intensities, and optionally the pulse rate, are greater than the average or maximal values expected for the lead operation in a body; optionally the electrical parameters vary during at least part of the test.

Figure 4:
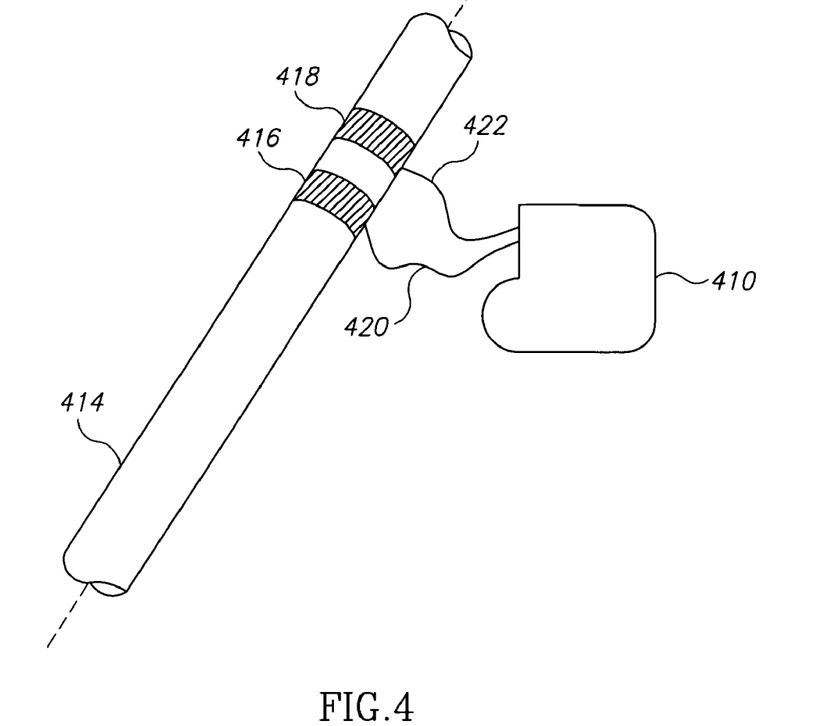
FIG. 4 is a schematic illustration of electrical connection of a bipolar lead as optionally used in an exemplary embodiment of the invention.

In an exemplary embodiment, an optional bipolar lead 414 has 2 electrical contacts 416 418 close to one end of the lead. The contacts are connected to an electrical generator 410 via respective wires 420 422.

Optionally and alternatively, lead is unipolar where either one of the contacts 416 or 418 and the respective wire are absent; optionally they are not connected in a bipolar lead. The electric circuit may be closed through the optional immersion solution, or by any other suitable method such as an auxiliary conductor.

Optionally the electrical generator 410 is a pulse generator; optionally the pulse generator is approximately equivalent to a one used in the lead operation in the body.

Optionally and/or additionally, at least part of the bending section of the lead is approximately maintained at a specific temperature during the test. Optionally, the temperature is approximately the temperature of the intended environment of the lead, for example at 37° C. or in the range of 36°-48° C.; optionally the temperature is higher than what is expected for the lead environment; optionally the temperature varies during at least part of the test Optionally and alternatively to turning the rollers on a lead with a non-skidding contact, the rollers, and optionally the lead, may be adapted for a substantially smooth slippage of the rollers on the lead, where the rollers may comprise only the respective bending sectors of the rollers (116a and 116b). Optionally rolling and slippage are used simultaneously or sequentially on substantially fixed or substantially rotating rollers.

Figure 5:
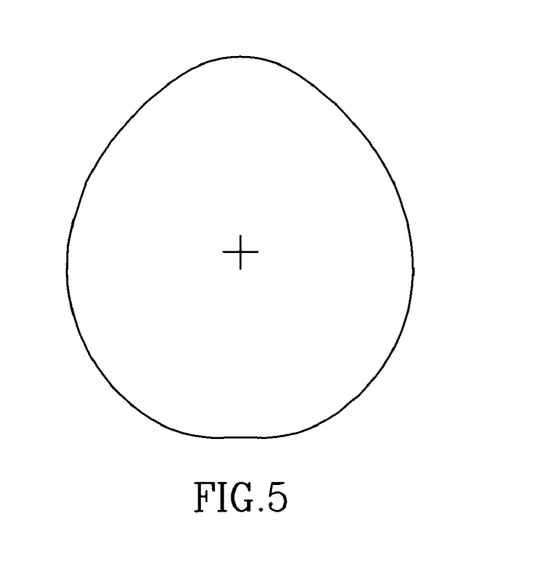
FIG. 5 is a schematic illustration of non-circular roller profile in accordance with an exemplary embodiment of the invention.

Optionally, the roller may have a circular or non-circular cross-section. An exemplary non-circular shape is depicted in FIG. 5.

Motor 130 is optionally an electric motor; optionally other movement devices and mechanisms may be used, not precluding a manual operation.

Figure 2:
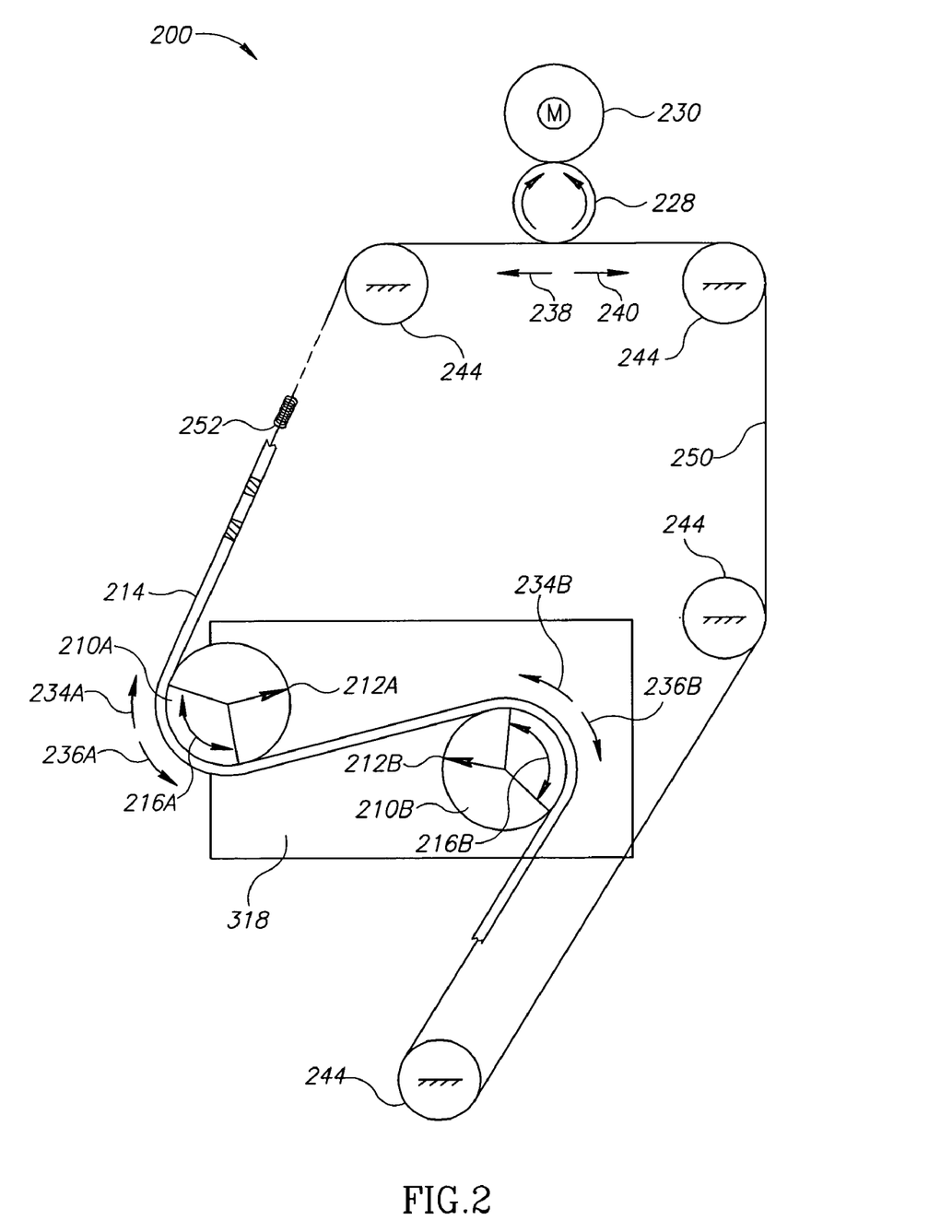
FIG. 2 is a schematic illustration of a mechanical apparatus for testing lead fatigue, in accordance with an exemplary embodiment of the invention where a lead section is moved over a bending roller.

FIG. 2 schematically illustrates another lead bending apparatus 200 according to an exemplary embodiment of the invention.

Exemplifying one or more rollers, rollers 210a and 210b with respective radii 212a and 212b are rotatably mounted on base 218. A lead 214 is wrapped about the rollers such that a segment of the lead is wrapped around sector 216a of roller 210a and another segment on sector 216b of roller 210b.

The lead, optionally with extensions appended to its ends, is included in a closed loop 250 supported by pulleys 244.

The lead is kept in sufficient tension to maintain a non-skid contact with the rollers by a tension element such as a spring 252, which is included in the loop.

The loop 250 is movable in directions 238 or 240 by motor 230 via a linkage member 228. When the lead moves, the rollers turn and compel the lead to bend and un-bend around sectors analogous to 216a and 216b. Specifically, as one part of the lead region comes in contact with a roller, it wraps and bends it while a corresponding part of the lead that leaves contact with the roller un-wraps from the roller contact and straightens.

As a roller moves, a bending and un-bending occur at successive positions along a section of the lead. These positions, corresponding to each roller, may coincide, at least partially, to comprise an extended bending section.

When loop 250 moves in directions 238, roller 210a rotates about direction 236a and roller 210b about direction 236b; when loop 250 moves in the opposite direction 240, roller 210a rotates in opposite direction 234a and roller 210b in opposite direction 234b.

Moving loop 250 in alternating directions 238 and 240 comprises a bending/un-bending cycle.

The bending/un-bending cycles may be repeated, the repetition comprising a fatigue test.

Optionally and alternatively, employing a plurality of rollers that simultaneously bend the lead in different directions, the loop with lead 214 may be moved in only one of the directions 238 or 240, wherein one pass will comprises a cycle, and successive looping cycles comprise a fatigue tests.

Optionally and additionally, the tension element 252 applies a force to maintain a greater tension in the lead than required for a non-skid contact with the rollers.

Optionally or alternatively, other methods or elements may be used to apply tension on the lead.

Optionally or alternatively, rather than using a closed loop, other methods or mechanisms may be used to move the lead in alternating directions about a roller sector.

Optionally, but not generally necessarily, the operations, options, provisions and considerations described for apparatus 100 of FIG. 1, apply as well, optionally with necessary variations, to apparatus 200 and its counter parts of FIG. 2. For example, lead 214, motor 230, electrical contacts and stimulation, immersion in solution, temperature, operational parameters, and such, and are not repeated for brevity.

Figure 3:
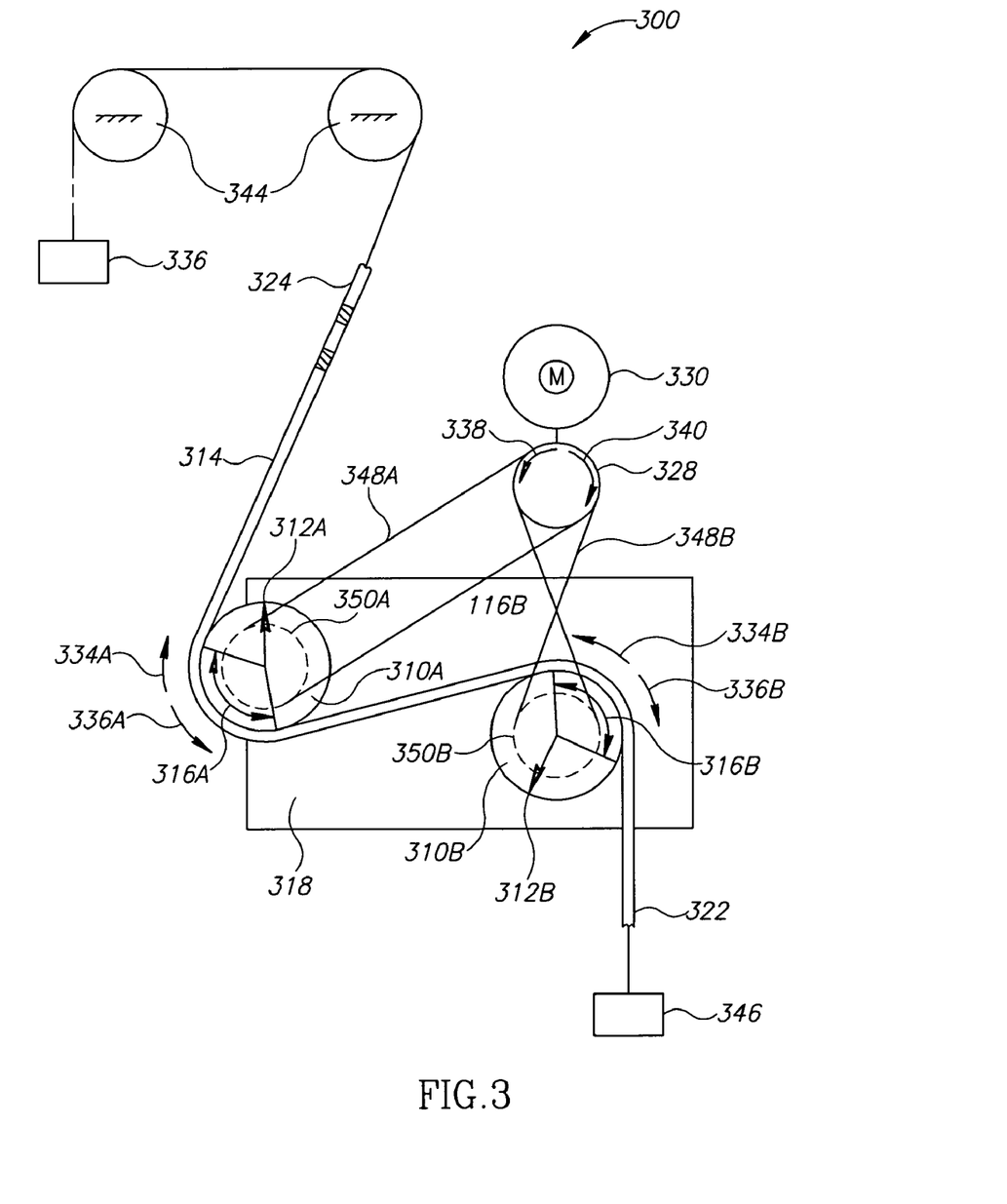
FIG. 3 is a schematic illustration of a mechanical apparatus for testing lead fatigue, in accordance with an exemplary embodiment of the invention where a bending roller is rotated.

FIG. 3 schematically illustrates another lead bending apparatus according to an exemplary embodiment of the invention.

Exemplifying one or more rollers, rollers 310a and 310b with respective radius 312a and 312b are rotatably mounted on frame 318. A lead 314 is wrapped about the rollers such that a segment of the lead is wrapped around sector 316a of roller 310a and another segment on sector 316b of roller 310b.

The lead is kept in sufficient tension to maintain a non-skid contact with the rollers by pulling one end 322 by weight 346 and pulling the other end 324 by a counter weight 336 via pulleys 344 the with suitable loads.

Motor 330 via linkage member 328 rotates the rollers by driving strips 348a and 348b, for example bands, belts, and chains. Optionally and additionally, other rotational motion transfer mechanisms may be used, such as gears.

When the rollers turn, they compel the lead to move and thus to bend and un-bend about sectors analogous to 316a and 316b. Specifically, as one part of the lead region comes in contact with a roller, it wraps and bends it while a corresponding part of the lead that leaves contact with the roller un-wraps from the roller contact and straightens.

As a roller turns, a bending and un-bending occur at successive position along a section of the lead. These positions, corresponding to each roller, may coincide, at least partially, to comprise an extended bending section.

When the driving strips 348a and 348b move in directions 338, roller 310a rotates about direction 336a and roller 310b about direction 336b; when the driving strips move in the opposite direction 340, roller 310a rotates in opposite direction 334a and roller 310b in opposite direction 334b.

Moving the driving strips in alternating directions 338 and 340 comprises a bending/un-bending cycle.

The bending/un-bending cycles may be repeated, the repetition comprising a fatigue test.

Optionally and additionally, the weights 336 and 346 carry loads to maintain a greater tension in the lead than required for a non-skid contact with the rollers. Alternatively and additionally, other devices may be used to apply the tension, such as elastic elements or springs.

Optionally and alternatively, other methods and appliances may be used to drive the rollers with respect to the lead. Optionally, lead 314 is secured at both ends to fixed bases and motor 330 is mounted on frame 318 such that when the rollers turn they move on the lead, compelling it to bend and unbend.

Optionally, but not necessarily, the operations, options, provisions and considerations described for apparatus 100 of FIG. 1, apply as well, optionally with necessary variations, to apparatus 300 and its counter parts of FIG. 3. For example, lead 314, motor 330, electrical contacts and stimulation, immersion in solution, temperature, operational parameters, and such, and are not repeated for brevity and clarity.

Figure 6:
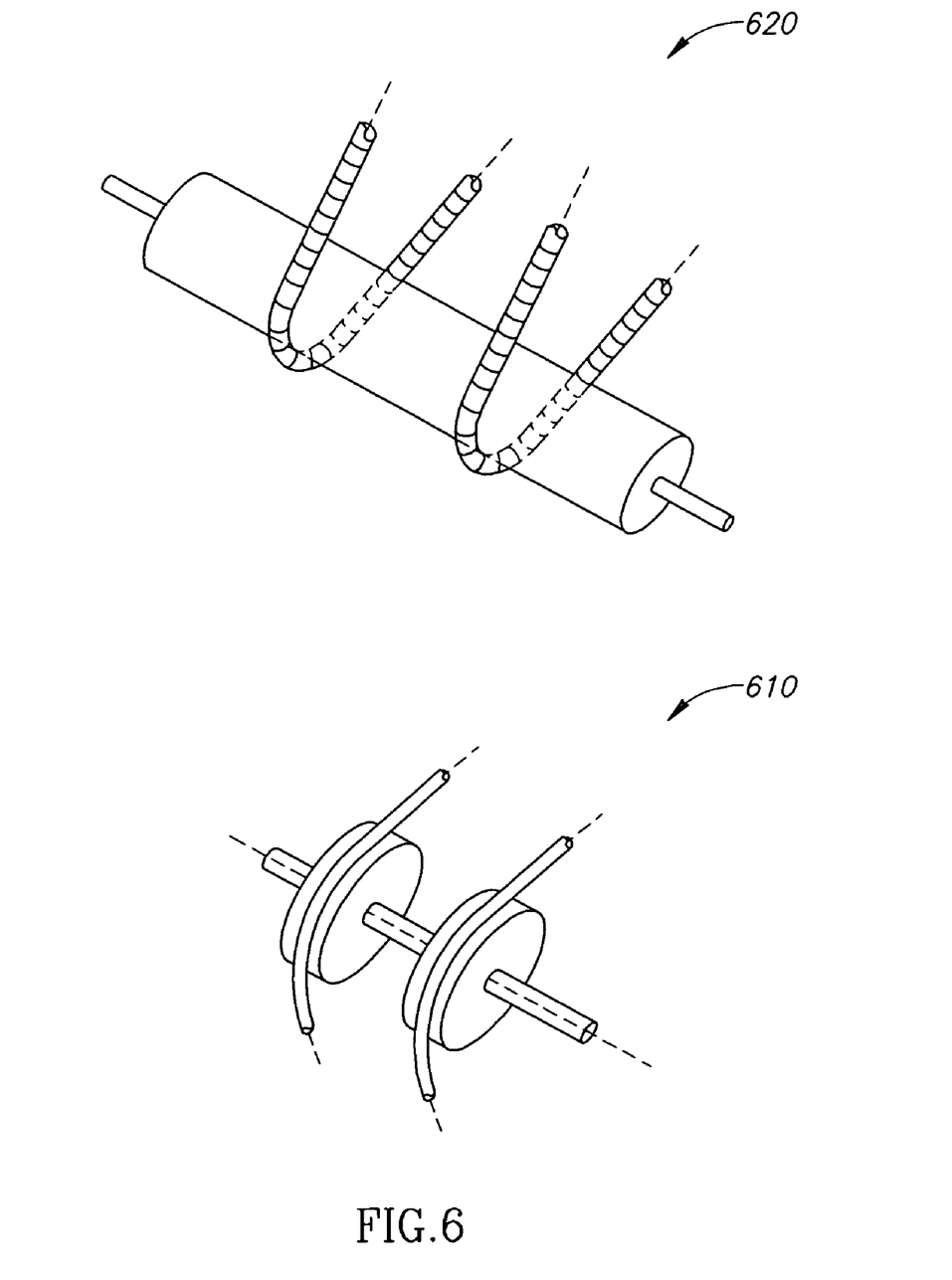
FIG. 6 is a schematic illustration of simultaneous bending of a plurality of leads, in accordance with exemplary embodiments of the invention.

In exemplary embodiments of the present invention, some of which are described above, a plurality of leads may be simultaneously tested. For example, by using a plurality of rollers with a common axis instead of a single roller or, alternatively and additionally, long rollers about which a plurality of leads are wrapped, as schematically illustrated as 610 and 620, respectively, in FIG. 6.

ILLUSTRATIVE EXAMPLE

The exemplary embodiment 100 of FIG. 1 was tested under the following partial list of conditions:
Lead length: ~35 cm
Electrical connection: Bipolar
Insulation material: Silicone rubber
Conductor: silver based core with titanium based shell
Bending radius to mid-line of lead: 6 mm
Temperature: 37° C.
Solution: 1.25 g/liter of NaCl
Rate of bending/un-bending: 2 cycles/second
Weight applying tension on lead: 200 gram
Electrical current delivery: Biphasic waveform of +15 mA for 6 millisecond, then −15 mA for 6 milliseconds for 2 sec followed by 0.1 second shorting and 1.9 seconds off.

The lead withstood the test up to about 1,000,000 cycles until the conduction was broken.

In the description and claims of the present application, each of the verbs "comprise", "include" and "have" as well as any conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to necessarily limit the scope of the invention. In particular, numerical values may be higher or lower than ranges of numbers set forth above and still be within the scope of the invention. The described embodiments comprise different features, not all of which are required in all embodiments of the invention. Some embodiments of the invention utilize only some of the features or possible combinations of the features. Alternatively and additionally, portions of the invention described/depicted as a single unit may reside in two or more separate physical entities which act in concert to perform the described/depicted function. Alternatively and additionally, portions of the invention described/depicted as two or more separate physical entities may be integrated into a single physical entity to perform the described/depicted function. Variations of embodiments of the present invention that are described and embodiments of the present invention comprising different combinations of features noted in the described embodiments can be combined in all possible combinations including, but not limited to use of features described in the context of one embodiment in the context of any other embodiment. The scope of the invention is limited only by the following claims.

All publications and/or patents and/or product descriptions cited in this document are fully incorporated herein by reference to the same extent as if each had been individually incorporated herein by reference.

What is claimed is:

1. A method for testing the fatigue of an implantable lead comprising:
    applying sufficient tension to the lead for maintaining non-skid contact with a roller; and
    simultaneously bending and un-bending the lead at a plurality of successive positions by moving at least one roller along said plurality of successive positions.

2. A method according to claim 1, wherein the bending and un-bending positions comprise a substantial length of the lead.

3. A method according to claim 1, wherein the bending and un-bending positions comprise approximately the extent of the lead length where bending is expected in the body.

4. A method according to claim 1, wherein the bending and un-bending positions comprise approximately 2 cm.

5. A method according to claim 1, wherein at least a portion of the lead subject to the bending and un-bending is immersed in a solution.

6. A method according to claim 5, wherein the solution concentration is approximately at least the expected concentration of the environment of the lead in the body.

7. A method according to claim 1, wherein the lead comprises at least one electrical contact and wherein voltage and current are applied to the lead at the contact.

8. A method according to claim 7, wherein the current amplitude waveform of said current may vary in time.

9. A method according to claim 8, wherein the current amplitude waveform of said current is approximately at least the expected amplitude waveform of electrical stimulation for the lead in the body.

10. A method according to claim 1, wherein at least part of the bending positions of the lead are maintained at a substantially controlled temperature.

11. A method according to claim 1, wherein
at least a part of the lead is wrapped about a sector of at least one roller, as the at least one roller moves along the lead, such that the lead successively wraps and bends at one end of a sector and simultaneously un-wraps and is straightened at the other end of the sector.

12. A method according to claim 11, wherein the motion is due to rotating a roller about a substantially fixed rotary axis against the lead such that successive positions of the lead come in contact with and leave contact with the roller.

13. A method according to claim 11, wherein the motion is due to rotating and moving the roller against a substantially tensile lead at a plurality of successive positions.

14. A method according to claim 11, wherein separate parts of the lead are wrapped about sectors of a plurality of respective rollers such that more than one portion of the lead is simultaneously bent/straightened.

15. A method according to claim 11, wherein a plurality of leads simultaneously bends and un-bend about at least one roller.

16. A method according to claim 11, wherein the relative motion between a lead and a roller comprises substantially a slippage motion.

17. A method according to claim 11, wherein said roller has a substantially circular cross-section.

18. A method according to claim 11, wherein said roller has a substantially non-circular cross-section.

19. An apparatus for fatigue test of an implantable lead, comprising:
at least one roller mounted on a frame;
a motor operative to move said frame such that a roller maintains a non-skid contact with a sufficiently tensile lead; and
a solution for immersing at least a part of the lead;
wherein said frame simultaneously bends and unbends the lead at a plurality of successive positions by moving said at least one roller along said plurality of successive positions.

20. An apparatus according to claim 19, wherein the lead is maintained with at least non-skid contact with a sector of the roller, and wherein the motor is operative to rotate the roller so that the roller moves the lead about a sector of the roller.

21. An apparatus according to claim 19, wherein the lead is maintained with at least non-skid contact with a sector of the roller, and wherein the motor is mounted on the frame and operative to rotate the roller so that the frame moves with the roller against a substantially tensile lead.

22. An apparatus according to claim 19, wherein a plurality of leads is simultaneously bending and un-bending at a plurality of successive positions.

23. An apparatus according to claim 19, wherein said roller has a substantially circular cross-section.

24. An apparatus according to claim 19, wherein said roller has a substantially non-circular cross-section.

25. An apparatus according to claim 19 wherein said roller is non-rotating.

26. An apparatus according to claim 19 wherein said lead is in slip motion relative to the roller.

27. An apparatus according to claim 19 wherein the solution is an isotonic saline solution.

* * * * *